(12) United States Patent
Cannard et al.

(10) Patent No.: US 9,448,127 B2
(45) Date of Patent: Sep. 20, 2016

(54) DEVICE FOR MEASURING PRESSURE FROM A FLEXIBLE, PLIABLE, AND/OR EXTENSIBLE OBJECT MADE FROM A TEXTILE MATERIAL COMPRISING A MEASUREMENT DEVICE

(75) Inventors: Francis Cannard, Beaune (FR); Bruno Diot, Mercurey (FR); Christophe Lavarenne, Saint Remy (FR); Anna Lavarenne, legal representative, Saint Remy (FR); Eva Lavarenne, legal representative, Saint Remy (FR); Nicolas Vuillerme, Francin (FR); Yohann Payan, Allevard (FR)

(73) Assignee: Francis Cannard, Beaune (FR)

( * ) Notice: Subject to any disclaimer, the term of this patent is extended or adjusted under 35 U.S.C. 154(b) by 145 days.

(21) Appl. No.: 13/979,582

(22) PCT Filed: Jan. 12, 2012
(Under 37 CFR 1.47)

(86) PCT No.: PCT/FR2012/050074
§ 371 (c)(1),
(2), (4) Date: Jan. 16, 2014

(87) PCT Pub. No.: WO2012/095608
PCT Pub. Date: Jul. 19, 2012

(65) Prior Publication Data
US 2014/0150573 A1 Jun. 5, 2014

(30) Foreign Application Priority Data
Jan. 13, 2011 (FR) .................................. 11 50283

(51) Int. Cl.
*G01L 1/18* (2006.01)
*B29C 65/00* (2006.01)
(Continued)

(52) U.S. Cl.
CPC .............. *G01L 1/18* (2013.01); *B29C 66/729* (2013.01); *B29C 66/7314* (2013.01); *D03D 15/00* (2013.01); *D03D 25/005* (2013.01); *A61B 2562/0247* (2013.01); *G01L 1/2231* (2013.01)

(58) Field of Classification Search
CPC ... G01L 1/2231; G01L 1/18; G01G 19/4142; B60R 21/015; B29C 66/729; B29C 66/7314; D03D 15/00; D03D 25/065
USPC ....................................... 73/862.627, 862.046
See application file for complete search history.

(56) References Cited

U.S. PATENT DOCUMENTS 6,155,120 A * 12/2000 Taylor ..................... 73/862.046
2002/0194934 A1* 12/2002 Taylor ..................... 73/862.046
(Continued)

FOREIGN PATENT DOCUMENTS

EP 1211633 A1 6/2002
WO 8701574 A1 3/1987
(Continued)

OTHER PUBLICATIONS

International Search Report and Written Opinion of the International Searching Authority Application No. PCT/FR2012/050074 Completed: Jun. 7, 2012; Mailing Date: Jul. 18, 2012 10 pages.

*Primary Examiner* — Lisa Caputo
*Assistant Examiner* — Nathaniel T Woodward
(74) *Attorney, Agent, or Firm* — St Onge Steward Johnson and Reens LLC

(57) ABSTRACT

A device and method for measuring the pressure exerted at different points of a flexible, pliable and/or extensible fabric capable of being worn as a garment, lapel, or the like, which provides three stacked layers including a first insulating layer comprising an arrangement of insulating fibers and at least one row of at least one conductive yarn in contact with a first surface of a piezoresistive layer of fibers of a piezoresistive material, and a second insulating layer comprising an arrangement of insulating fibers, including at least one row of at least one conductive yarn, in contact with a second surface of the piezoresistive layer, and an electronic circuit capable of measuring the electric resistance variation when a pressure is exerted on the fabric, the pressure being a function of the resistance variation.

22 Claims, 2 Drawing Sheets

(51) Int. Cl.
 *D03D 15/00* (2006.01)
 *D03D 25/00* (2006.01)
 *G01L 1/22* (2006.01)

(56) References Cited

U.S. PATENT DOCUMENTS

2004/0168479 A1* 9/2004 McMurray ............... 66/202

2009/0128168 A1 5/2009 Qi et al.

FOREIGN PATENT DOCUMENTS

| WO | 0175778 A1 | 10/2001 |
| WO | 2005096133 A1 | 10/2005 |
| WO | 2009023937 A1 | 2/2009 |

* cited by examiner

DEVICE FOR MEASURING PRESSURE FROM A FLEXIBLE, PLIABLE, AND/OR EXTENSIBLE OBJECT MADE FROM A TEXTILE MATERIAL COMPRISING A MEASUREMENT DEVICE

BACKGROUND

The present invention relates to a device of pressure measurement from a pliable or pliable object such as a fabric, for example, which is particularly adapted to a pressure measurement to prevent the occurrence of pressure ulcers in people suffering from chronic diseases, for example, a loss of mobility or of sensitivity.

BACKGROUND OF THE INVENTION

It is well known that measuring the pressure, and more generally the distribution of forces on a determined surface, may be achieved by means of so-called capacitive pressure sensors. Said capacitive pressure sensors comprise one or several capacitive cells which are appropriately arranged on the sensor contact surface. Each capacitive cell comprises a pair of panels obtained in an electrically-conductive material and a layer of insulating or dielectric material positioned between the conductive panels.

The pressure acting on the capacitive sensor cells is measured by measuring the capacitance variation of the capacitive cells caused by the variation of the distance between the conductive panels having a pressure exerted thereon.

This is especially featured in European patent application EP 1211633, which describes a device for measuring the pressure distribution on a surface.

Pressure measurement devices comprising so-called resistive pressure sensors are also known.

This is especially featured in U.S. Pat. No. 6,155,120, which describes a method and a device for measuring the pressure of a foot by means of the variation of the piezoresistance. Said device comprises a rectangular array of piezoresistive force sensors enclosed within a thin polymer envelope which is introduced into a shoe, or which is incorporated to a sock likely to be worn on a foot or on a hoof. The preferred embodiment of the invention uses piezoresistive elements for detecting pressures or normal forces, which comprise a polymer fabric mesh impregnated with conductive particles in suspension in an elastomeric vehicle, preferably silicon rubber. The meshed piezoresistive layer is sandwiched between an array of row and column conductor strip laminations, preferably formed of a Nylon® mesh impregnated with printed metal tracks. In a variation of the basic embodiment, each normal force detection element is bordered with pairs of shear force detection elements, arranged laterally and longitudinally, each of the shear force detection elements comprising a pair of adjacent resilient piezoresistive pads which have lateral surfaces in longitudinal contact. Such pads are slidably moveable, and when urged into more or less intimate contact as a response to shear forces directed perpendicularly to their tangent contact plane, the electric resistance between pads varies in a predetermined way as a function of the shear forces.

This is also featured in international patent application WO 87/01574, which describes a detection mat. Said detection mat is formed of support means, of an upper layer, of an intermediate layer, and of a lower layer which are attached to one another. The upper layer is formed of a flexible printed circuit having conductive tracks deposited on its lower surface. The intermediate layer is formed of a conductive rubber sheet and the lower layer is formed of a rigid printed circuit having conductive tracks deposited on its upper surface.

US patent application 2009/0128168 is also known, which describes multifunctional conductive polymer structures, and more specifically the use of conductive polymers as sensors in distributed detection systems, as sensors and actuators in multifunctional devices, and for multifunctional fabrics comprising such conductive polymers for controlling humidity, breathing, heart rate, blood pressure, skin temperature, weight and motions, in a sensor system integrated to garments, for example. A fabric comprising conductive polyaniline fibers which may be used both to distribute energy in a resistive heating and to measure the fabric temperature is described as an example of a multifunctional fabric sensor. In an alternative embodiment, a fabric comprising polyaniline fibers for forming a pressure sensor is described, the pressure being directly deduced from the resistance variation of the polyaniline fibers.

All these devices comprising capacitive or resistive sensors have the disadvantage of having a low flexibility, which considerably limits their field of application, such devices being insufficiently comfortable to be used in garments, for example. Further, such devices have high manufacturing costs, due to the use of specific means of production, which are incompatible with a large-scale distribution, and the pressure measured by capacitive sensors depends on ambient phenomena such as temperature and/or humidity.

To overcome some of these disadvantages, pressure sensors capable of being used in garments or the like have already been devised. This is especially featured in patent applications WO 2005/096133 and WO 2009/023937.

Document WO 2005/096133 describes a textile touch sensor which comprises a first and a second external conductive layers and a third intermediate layer between the first and the second conductive layers, said third intermediate layer being made of a non-conductive textile coated with a piezoresistive material. The first and second external conductive layers are made of a polyester fabric coated with polypyrrole, for example.

Document WO 2009/023937 (D3) describes a system and a garment that incorporate sensors for measuring the pressure or the force which is exerted on feet, on stumps equipped with prostheses, or on any other body part submitted to forces due to the situation. This document especially describes a sock where at least one section of the sock fabric is coated with a conductive polymer having conductive silver yarns sewn thereon.

Such sensors have the disadvantage of losing their measurement efficiency along time, and more specifically along successive washings of the garments or the like. Indeed, the conductive layers are deposited on the fabric or the like by coating. Now, successive washings alter these conductive layers, thus making measurements less accurate. Further, such pressure sensors would be immediately deteriorated in case of high temperature cleaning to sterilize the garment and its sensors, which sterilization is indispensable for a use of such pressure sensors in hospitals.

Such sensors also have the disadvantage of not being able to use means of production allowing a production and costs compatible with a wide distribution. The used manufacturing means require a large number of manual operations, which reduce the field of application to laboratory manipulations.

SUMMARY OF THE INVENTION

One of the aims of the invention thus is to overcome these disadvantages by providing a device for measuring the pressure distribution on a flexible or pliable surface such as a fabric, for example, of simple design and low cost, providing a pressure measurement independent from ambient phenomena such as temperature and/or humidity present at the fabric surface and providing a good resistance to frequent washings of the fabric.

For this purpose, the invention provides a device for measuring the pressure exerted at different points of a flexible, pliable and/or extensible fabric capable of being worn as a garment, lapel, or the like; said device is remarkable in that it comprises at least three stacked layers, a first insulating layer obtained from an arrangement of insulating fibers, comprising at least one row of at least one conductive yarn in contact with a first surface of a piezoresistive layer made of a piece of fabric formed of fibers made of a piezoresistive material, and a second insulating layer also obtained from an arrangement of insulating fibers, comprising at least one row of at least one conductive yarn, in contact with the opposite surface of the piezoresistive layer, and an electronic circuit capable of measuring the electric resistance variation when a pressure is exerted on the fabric, the pressure being a function of the resistance variation.

Preferably, the piezoresistive layer is obtained by knitting, weaving, or the like of fibers made of a piezoresistive material.

Advantageously, the piezoresistive layer comprises piezoresistive areas and insulating areas.

Preferably, the insulating layers are obtained by knitting, weaving, or the like of fibers made from an insulating material.

Further, the conductive yarns of the first insulating layer in contact with the first surface of the piezoresistive layer cross the conductive yarns of the second insulating layer in contact with the opposite surface of the piezoresistive layer.

Said conductive yarns of the first insulating layer in contact with the first surface of the piezoresistive layer extend perpendicularly to the conductive yarns of the second insulating layer in contact with the opposite surface of the piezoresistive layer.

Further, the piezoresistive material is an intrinsic conducting polymer (ICP) and/or an organic material, and preferably polyaniline and/or polypyrrole and/or carbon nanotubes.

Said conductive yarns are silver and/or nickel yarns.

Further, the electric circuit comprises means for measuring the electric resistance variation from the scanning of the sensor array, considering the conductive yarns of the upper insulating layer in contact with a surface of the piezoresistive layer and the conductive yarns of the lower insulating layer in contact with the other surface of the piezoresistive layer, the scanning being obtained from the sequential selection of a conductive yarn of the upper layer and the sequential reading of a conductive yarn of the lower layer crossing the conductive yarn of the upper layer, the reading of the sensor resistance variation being obtained from an analog-to-digital converter.

Another object of the invention relates to a pressure sensor capable of being connected to an electronic circuit measuring the electric resistance variation when a pressure is exerted on the sensor, the pressure being a function of the resistance variation; said sensor is remarkable in that it comprises at least three stacked layers, a first insulating layer, obtained from an arrangement of insulating fibers, comprising at least one row of at least one conductive yarn in contact with a first surface of a piezoresistive layer made of a piece of fabric formed from fibers made of a piezoresistive material, and a second insulating layer also obtained from an arrangement of insulating fibers, comprising at least one row of at least one conductive yarn, in contact with the opposite surface of the piezoresistive layer.

Preferably, the piezoresistive layer is obtained by knitting, weaving, or the like of fibers made of a piezoresistive material.

Advantageously, the piezoresistive layer comprises piezoresistive areas and insulating areas.

Preferably, the insulating layers are obtained by knitting, weaving, or the like of fibers made of an insulating material.

Said conductive yarns of the first insulating layer in contact with the first surface of the piezoresistive layer extend perpendicularly to the conductive yarns of the second insulating layer in contact with the opposite surface of the piezoresistive layer.

Further, the piezoresistive material is an intrinsically conducting polymer (ICP) and/or an organic metal, and preferably polyaniline and/or polypyrrole and/or carbon nanotubes.

Said conductive yarns are silver and/or nickel yarns.

A last object of the invention relates to a method for manufacturing at least one pressure sensor capable of being connected to an electronic circuit measuring the electric resistance variation when a pressure is exerted on the sensor, the pressure being a function of the resistance variation; said method is remarkable in that it comprises at least the steps of:
  forming a first insulating layer obtained from an arrangement of insulating fibers and comprising at least one row of at least one conductive yarn;
  forming a piezoresistive layer,
  forming a second insulating layer also obtained from an arrangement of insulating fibers and comprising at least one row of at least one conductive yarn; and
  assembling the two insulating layers and the piezoresistive layer in such a way that the row(s) of conductive yarns of the first insulating layer is (are) in contact with a first surface of the piezoresistive layer and that the row(s) of conductive yarns of the second insulating layer is (are) in contact with the opposite surface of said piezoresistive layer.

The step of assembling the insulating layers and the piezoresistive layer comprises bonding said layers.

As a variation, the insulating layers and the piezoresistive layers are simultaneously formed by a 3-dimensional knitting or weaving, the piezoresistive layer being formed by so-called spacer yarns connecting the two insulating layers at the level of the conductive yarns of the insulating layers.

According to another alternative embodiment of the method according to the invention, at least one of the insulating layers is knit from an arrangement of insulating fibers while leaving rows empty, after which a third insulating layer comprising rows of conductive yarns spaced apart by a distance substantially equal to the spacing between the empty rows of the insulating layer is assembled with said insulating layer so that the conductive yarns extend in the empty rows and are in contact with the piezoresistive layer.

BRIEF DESCRIPTION OF THE DRAWINGS

The foregoing and other features and advantages of the present invention will be discussed in detail in the following non-limiting description of specific embodiments of the pressure measurement device according to the invention, in connection with the accompanying drawings, among which.

DETAILED DESCRIPTION

Figure 1:
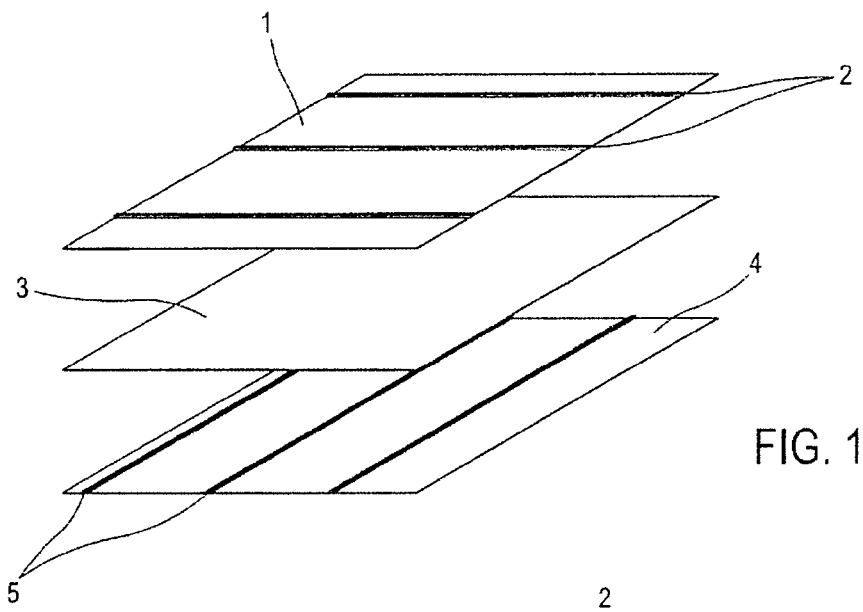
FIG. 1 is a simplified perspective representation of the pressure measurement device according to the invention.
Figure 2:
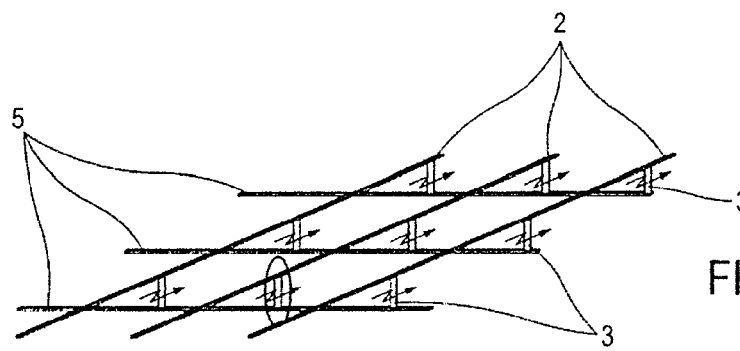
FIG. 2 is a simplified perspective representation of the sensors of the pressure measurement device according to the invention.
Figure 3:
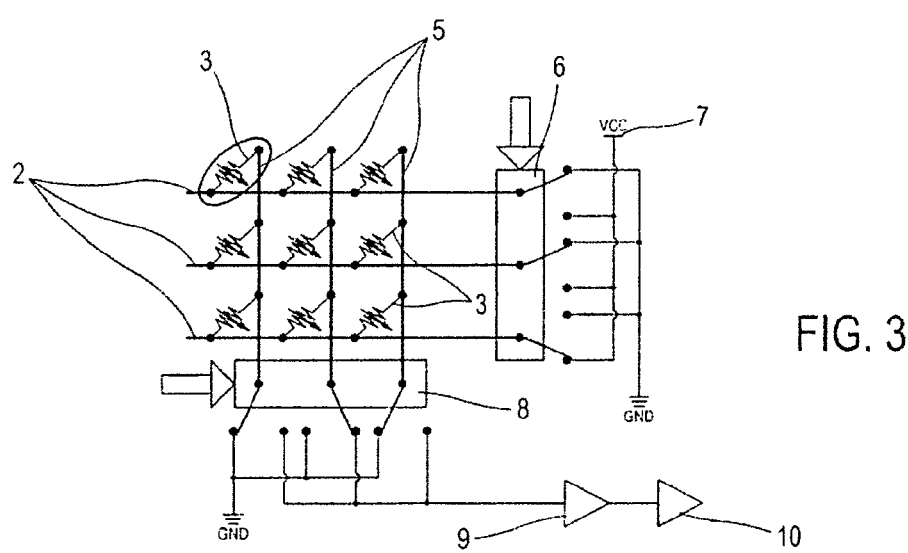
FIG. 3 is a simplified representation of the electric circuit of the pressure measurement device according to the invention shown in FIGS. 1 and 2.

Referring to FIGS. 1 to 3, the pressure measurement device according to the invention is formed of at least three stacked pieces of fabric, a first piece of insulating fabric 1, made of cotton, nylon, or any other flexible insulating material, comprising rows of conductive yarns 2, attached to a first surface of a so-called piezoresistive fabric piece 3, and a second piece of insulating fabric 4, also made of cotton, nylon, or any other flexible insulating material, comprising rows of conductive yarns 5, attached to the opposite surface of piezoresistive fabric piece 3. Piezoresistive fabric piece 3 for example is a piece of fabric manufactured with fibers made of a piezoresistive material, preferably an intrinsically conducting polymer (ICP) and/or an organic metal such as polyaniline (PANI) sold by ORMECON™, for example, and/or polypyrrole (PPY), for example, and/or carbon nanotubes. Said piezoresistive fabric piece 3 may be obtained by knitting, weaving, or the like or by coating or by projection of a piezoresistive material or by any other method well known by those skilled in the art. Similarly, insulating fabric pieces 1 and 4 may be obtained by knitting, weaving, braiding or the like of fibers made from an insulating material.

Said conductive yarns 2 of first insulating fabric piece 1 in contact with a first surface of piezoresistive fabric 3 extend substantially perpendicularly to conductive yarns 5 of second insulating fabric piece 4 in contact with the opposite surface of piezoresistive fabric 3, thus forming a pressure sensor array.

It should be observed that conductive yarns 2 of first insulating fabric piece 1 in contact with the first surface of piezoresistive fabric 3 may extend according to any angle with respect to conductive yarns 5 of second insulating fabric piece 4 in contact with the opposite surface of resistive piezoresistive fabric 3, the important point being that said conductive yarns 2 of first insulating fabric piece 1 and conductive yarns 5 of second insulating fabric piece 4 cross, while remaining within the spirit and scope of the invention.

Further, referring to FIG. 3, conductive yarns 2 of first insulating fabric piece 1 in contact with a first surface of piezoresistive fabric 3 are connected by any appropriate means well known by those skilled in the art to a first bus 6 connected to a power supply source 7 in such a way that conductive yarns 2 are selectively powered. Conductive yarns 5 of second insulating fabric piece 4 in contact with the opposite surface of piezoresistive 3 fabric are connected by any appropriate means to a second bus 8 selectively collecting the resistance variation created by the piezoresistive material when a pressure is exerted on a determined surface of the fabric. Said second bus 8 is connected to an analog interface 9 connected to an A/D (Analog-to-Digital) converter 10 for the processing of the measured data.

Figure 4:
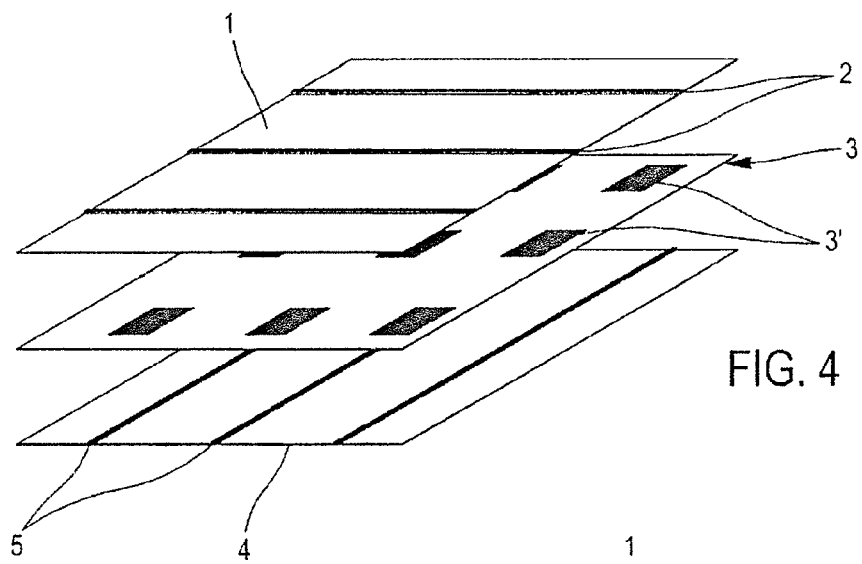
FIG. 4 is a simplified perspective representation of an alternative embodiment of the pressure measurement device according to the invention.

According to a first alternative embodiment of the device according to the invention, referring to FIG. 4, said device comprises, as previously, at least three stacked pieces of fabric, a first insulating fabric piece 1, made of cotton, nylon, or any other flexible insulating material, comprising rows of conductive yarns 2, attached to a first surface of a so-called piezoresistive fabric piece 3, and a second piece of insulating fabric 4, also made of cotton, nylon, or any other flexible insulating material, comprising rows of conductive yarns 5, attached to the opposite surface of piezoresistive fabric piece 3. Piezoresistive fabric piece 3 for example is a piece of fabric manufactured with fibers made from a piezoresistive material, preferably an intrinsically conducting polymer (ICP) and/or an organic metal such as polyaniline (PANI) sold by ORMECON™, for example, and/or polypyrrole (PPY), for example, and/or carbon nanotubes. Said piezoresistive fabric piece 3 may be obtained by knitting, weaving, or the like or by coating or by projection of a piezoresistive material or by any other method well known by those skilled in the art.

This device differs from the previous one by the fact that so-called piezoresistive fabric piece 3 is also made from insulating fibers such as cotton, nylon, or the like, so that said piezoresistive fabric piece comprises piezoresistive areas 3' and insulating areas.

Said conductive yarns 2 of first insulating fabric piece 1 in contact with a first surface of piezoresistive fabric 3 extend substantially perpendicularly to conductive yarns 5 of second insulating fabric piece 4 in contact with the opposite surface of piezoresistive fabric 3 at the level of piezoresistive areas 3', thus forming a pressure sensor array.

In this specific embodiment, piezoresistive areas 3' are square; however, it should be obvious that said piezoresistive areas 3' may have any shape, size, and location while remaining within the scope of the invention.

Figure 5:
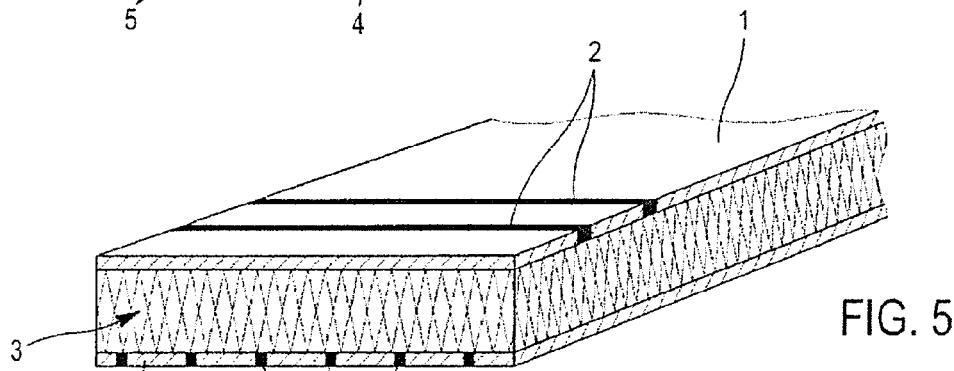
FIG. 5 is a simplified perspective representation of a second alternative embodiment of the pressure measurement device according to the invention.

According to a second alternative embodiment of the device according to the invention, referring to FIG. 5, said device comprises, as previously, at last three stacked pieces of fabric, a first piece of insulating fabric 1, made of cotton, nylon, or any other flexible insulating material, comprising rows of conductive yarns 2, attached to a first surface of a so-called piezoresistive fabric piece 3, and a second piece of insulating fabric 4, also made of cotton, nylon, or any other flexible insulating material, comprising rows of conductive yarns 5, attached to the opposite surface of piezoresistive fabric piece 3.

Insulating layers 1, 4 and piezoresistive layer 3 are simultaneously formed by 3-dimensional (3D) knitting or weaving, by means of any machine, commonly called loom, well known by those skilled in the art, insulating layers 1, 4 forming the external layers of the 3D fabric, and piezoresistive layer 3 being formed by so-called spacer yarns connecting the two insulating layers at the level of conductive yarns 2, 5 of insulating layers 1, 4.

It should be obvious that piezoresistive layer 3 formed by 3D knitting or weaving may comprise, as previously, piezoresistive areas (3') having any shape, such as a square shape, for example, and insulating areas, to form an array of pressure sensors while remaining within the spirit and scope of the invention.

Figure 6:
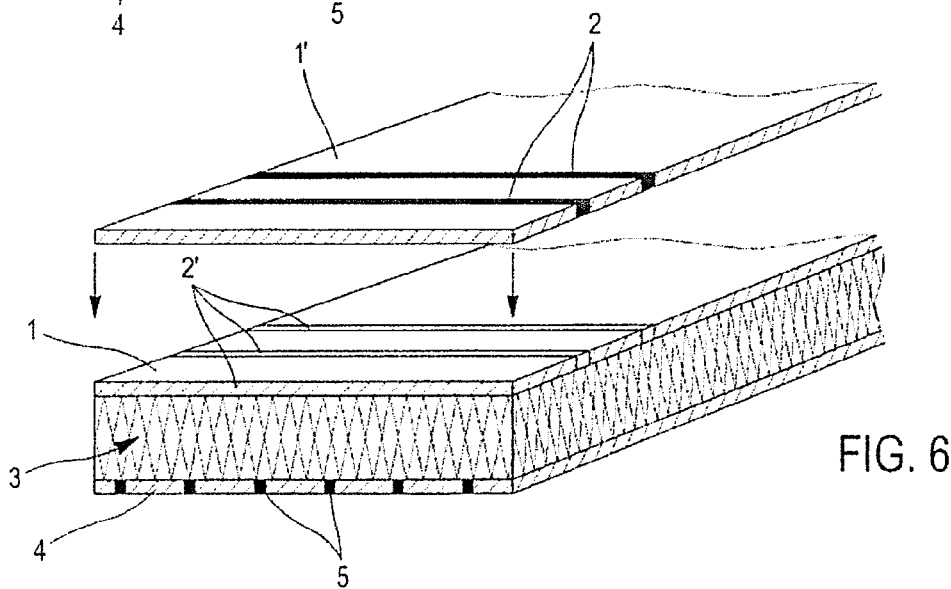
FIG. 6 is a simplified representation of the different manufacturing steps of the second alternative embodiment of the pressure measurement device according to the invention shown in FIG. 5.

Since most looms enabling to form 3D fabrics are not capable of simultaneously forming insulating layers 1, 4 comprising conductive yarns respectively in the weft direction and in the warp direction, the sensor according to the invention may be formed in three steps, in relation with FIG. 6. In a first step, insulating layers 1, 4 and piezoresistive layer 3 are simultaneously formed by 3-dimensional knitting or weaving, piezoresistive layer 3 being made of piezoresistive so-called spacer yarns interconnecting insulating layers 1, 4 at the level of conductive yarns 2, 5 of insulating layers 1, 4. At least one of insulating layers 1 is knit from an arrangement of insulating fibers while leaving empty rows 2' after which, in a second step, a third insulating layer 1' comprising rows of conductive yarns 2 separated by a distance substantially equal to the spacing between empty rows 2' of insulating layer 1 is formed. In a third and last step, third insulating layer 1' is assembled with said insulating layer 1 so that conductive yarns 2 extend in empty rows 2' and are in contact with piezoresistive layer 3. The assembly may be performed in any appropriate way well known by those skilled in the art such as by bonding, for example.

Secondarily, the previously-described electric circuit may advantageously be connected to a processor, such as the processor of a PC-type computer or the like, performing the pressure analysis and including methods enabling to process applications, and to means enabling to send the data measured from the sensors and the result of the processing operations. Said data transmission means may comprise any wire or wireless transmission means such as wi-fi®, bluetooth®, RFID or the like, well known by those skilled in the art.

It should be noted that the device according to the invention will find a large number of applications for sensors capable of taking various shapes. Their flexibility and their comfort allow a special use thereof in measuring pressures around the human body. They may for example be used to measure excessive pressures which might cause the occurrence of pressure ulcers, particularly on soft surfaces such as cushions or hospital beds; but also between the body and a scoliosis corset. Given that such sensitive textiles can be easily integrated to garments, they may equip a pressure-sensitive undergarment or garment such as socks, for example, which analyze plantar pressures as well as pressures exerted around the foot.

It should be understood that insulating layers 1 and 4, especially, may comprise a single row of conductive yarns 2, 5 and that each row may comprise a single conductive yarn 2, 5, while remaining within the spirit and scope of the invention.

Finally, it should be obvious that the examples which have just been given are specific illustrations only and by no means limiting in terms of field of application of the invention.

The invention claimed is:

1. A pressure sensor, capable of being connected to an electronic circuit measuring an electric resistance variation when a pressure is exerted on the pressure sensor, the pressure being a function of the electric resistance variation, wherein the pressure sensor comprises at least three stacked continuous layers defining an array of sensor elements and including:
   a single continuous piezoresistive layer comprising fibers of a piezoresistive material,
   a first continuous insulating layer comprising an arrangement of insulating fibers and a plurality of rows of at least one conductive yarn in contact with a single first surface of the continuous piezoresistive layer, and
   a second continuous insulating layer comprising an arrangement of insulating fibers and a plurality of rows of at least one conductive yarn in contact with a single second surface of the continuous piezoresistive layer, and
   wherein each one of the sensor elements is formed at a crossing between one conductive yarn of the first continuous insulating layer in contact with the single second surface of the continuous piezoresistive layer and one conductive yarn of the second continuous insulating layer in contact with the single second surface of the continuous piezoresistive layer.

2. The pressure sensor of claim 1, wherein the continuous piezoresistive layer is obtained by knitting or weaving of fibers of a piezoresistive material.

3. The pressure sensor of claim 1, wherein the continuous piezoresistive layer comprises piezoresistive areas and insulating areas.

4. The pressure sensor of claim 1, wherein the continuous insulating layers are obtained by knitting or weaving of fibers made of an insulating material.

5. The pressure sensor of claim 1, wherein the piezoresistive material is an intrinsically conducting polymer such as polyaniline, and/or polypyrrole, and/or an organic metal, and/or carbon nanotubes.

6. The pressure sensor of claim 1, wherein the conductive yarns comprise silver or nickel yarns.

7. A device for measuring the pressure exerted at different points of a flexible, pliable, and/or extensible fabric capable of being worn as a garment or lapel, wherein the device comprises:
   an electronic circuit capable of measuring the electric resistance variation when a pressure is exerted on the fabric, the pressure being a function of the electric resistance variation, and
   a pressure sensor capable of being connected to the electronic circuit, wherein the pressure sensor comprises at least three stacked continuous layers defining an array of sensor elements and including a single continuous piezoresistive layer comprising fibers of a piezoresistive material, a first continuous insulating layer comprising an arrangement of insulating fibers and a plurality of rows of at least one conductive yarn in contact with a single first surface of the continuous piezoresistive layer, and a second continuous insulating layer comprising an arrangement of insulating fibers and a plurality of rows of at least one conductive yarn in contact with a single second surface of the continuous piezoresistive layer, and
   wherein each one of the sensor elements is formed at a crossing between one conductive yarn of the first continuous insulating layer in contact with the single second surface of the continuous piezoresistive layer and one conductive yarn of the second continuous insulating layer in contact with the single second surface of the continuous piezoresistive layer.

8. The device of claim 7, wherein the continuous piezoresistive layer is obtained by knitting or weaving the fibers of a piezoresistive material.

9. The device of claim 7, wherein the continuous piezoresistive layer comprises piezoresistive areas and insulating areas.

10. The device of claim 7, wherein the continuous insulating layers are obtained by knitting or weaving of fibers made of an insulating material.

11. The device of claim 7, wherein the conductive yarns of the first continuous insulating layer in contact with the single first surface of the continuous piezoresistive layer cross the conductive yarns of the second continuous insulating layer in contact with the single second surface of the continuous piezoresistive layer.

12. The device of claim 11, wherein the conductive yarns of the first continuous insulating layer in contact with the single first surface of the continuous piezoresistive layer extend perpendicularly to the conductive yarns of the second continuous insulating layer in contact with the single second surface of the continuous piezoresistive layer.

13. The device of claim 7, wherein the piezoresistive material is an intrinsically conducting polymer and/or an organic metal, and/or carbon nanotubes.

14. The device of claim 7, wherein the piezoresistive material is polyaniline.

15. The device of claim 7, wherein the piezoresistive material is polypyrrole.

16. The device of claim 7, wherein the conductive yarns comprise silver yarns.

17. The device of claim 7, wherein conductive yarns comprise nickel yarns.

18. The device of claim 7, wherein the electronic circuit measures the electric resistance variation from the scanning of a sensor array, considering the conductive yarns of the first continuous insulating layer in contact with the single first surface of the continuous piezoresistive layer and the conductive yarns of the second continuous insulating layer in contact with the single second surface of the continuous piezoresistive layer, the scanning being obtained from the sequential selection of a conductive yarn of the first continuous insulating layer and the sequential reading of a conductive yarn of the second continuous insulating layer crossing the conductive yarn of the first continuous insulating layer, the reading of the sensor resistance variation being obtained from an analog-to-digital converter.

19. A method for manufacturing at least one pressure sensor capable of being connected to an electronic circuit measuring an electric resistance variation when a pressure is exerted on the pressure sensor, the pressure being a function of the electric resistance variation, wherein the method comprises at least the steps of:
 forming a first continuous insulating layer comprising an arrangement of insulating fibers and a plurality of rows of at least one conductive yarn;
 forming a single continuous piezoresistive layer comprising fibers of a piezoresistive material,
 forming a second continuous insulating layer comprising an arrangement of insulating fibers and a plurality of rows of at least one conductive yarn, and
 assembling the first and second continuous insulating layers and the continuous piezoresistive layer in such a way that the rows of conductive yarns of the first continuous insulating layer are in contact with a single first surface of the continuous piezoresistive layer and that the rows of conductive yarns of the second continuous insulating layer are in contact with a single second surface of the continuous piezoresistive layer.

20. The method of claim 19, wherein the step of assembling the first and second continuous insulating layers and the continuous piezoresistive layer comprises bonding said continuous layers.

21. The method of claim 19, wherein the continuous insulating layers and the continuous piezoresistive layer are simultaneously formed by a 3-dimensional knitting or weaving, the continuous piezoresistive layer being formed by spacer yarns connecting the first and second continuous insulating layers at the level of the conductive yarns of the first and second continuous insulating layers.

22. The method of claim 21, wherein at least one of the first and second continuous insulating layers is knit from an arrangement of insulating fibers while leaving empty rows, then assembled with a third insulating layer comprising rows of at least one conductive yarn spaced apart by a distance substantially equal to the spacing between the empty rows so that the conductive yarns of the third insulating layer extend in the empty rows and are in contact with the continuous piezoresistive layer.

* * * * *